United States Patent [19]

Barchas et al.

[11] Patent Number: 4,490,363

[45] Date of Patent: Dec. 25, 1984

[54] METORPHAMIDE—A NOVEL MORPHINE-LIKE PEPTIDE

[75] Inventors: Jack D. Barchas, Stanford; Eckard Weber; Christopher J. Evans, both of Palo Alto, all of Calif.

[73] Assignee: Board of Trustees of The Leland Stanford Junior University Stanford Univ., Stanford, Calif.

[21] Appl. No.: 508,140

[22] Filed: Jun. 24, 1983

[51] Int. Cl.³ .................... A61K 37/00; C07C 103/52
[52] U.S. Cl. ............................... 424/177; 260/112.5 E
[58] Field of Search .................. 424/177; 260/112.5 E

[56] References Cited

PUBLICATIONS

European Journal of Pharmacology 85, (1982), 355–356.
Proc. Natl. Acad. Sci. 78, (1981), 1962–1966.

*Primary Examiner*—Delbert R. Phillips
*Attorney, Agent, or Firm*—Flehr, Holbach, Test, Albritton & Herbert

[57] ABSTRACT

A morphine-like amidated opioid octapeptide metorphamide having the structure Try-Gly-Gly-Phe-Met-Arg-Arg-Val-$NH_2$ has been isolated from bovine caudate nucleus extracts and synthesized by solid phase peptide synthesis methods. Metorphamide is thus far the only natural opioid peptide having a high $\mu$-binding activity.

3 Claims, 2 Drawing Figures

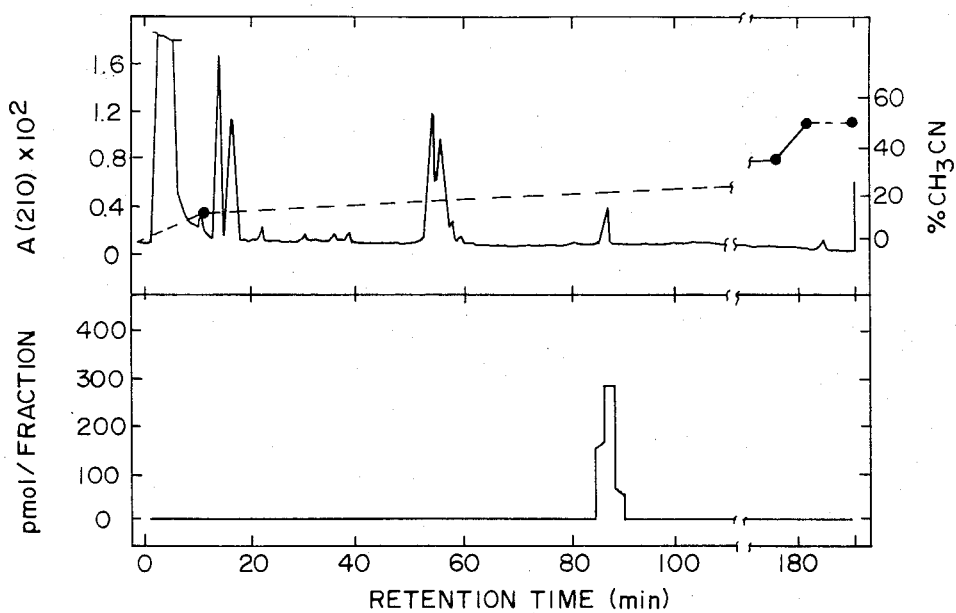
FIG.—1
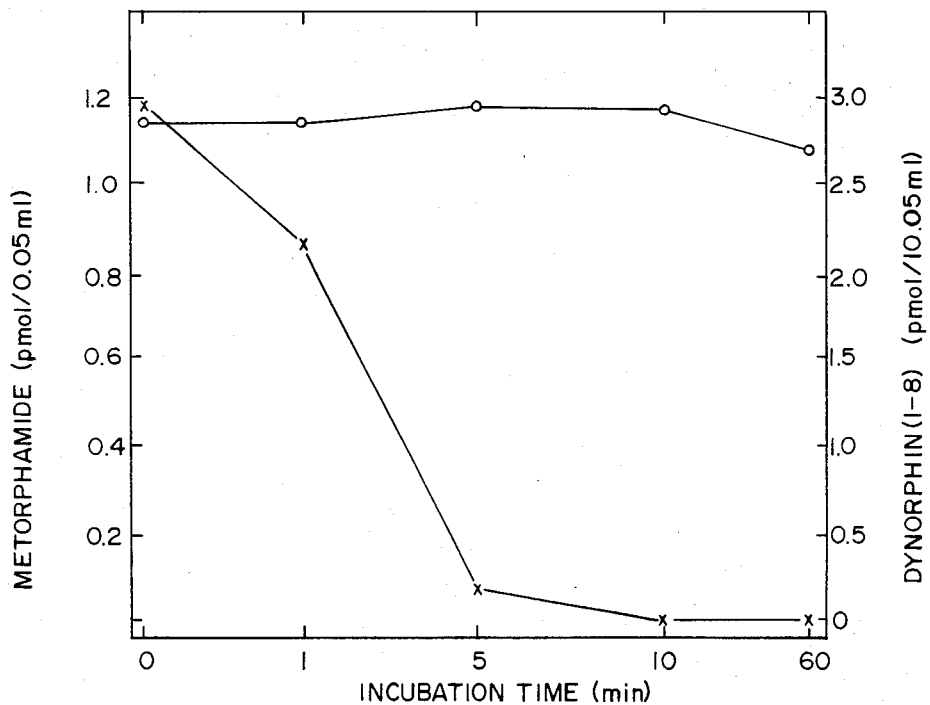
FIG.—2

METORPHAMIDE—A NOVEL MORPHINE-LIKE PEPTIDE

The present invention is directed to a novel peptide having morphine-like activity. In particular, the present invention is directed to a novel octapeptide having the structure Tyr-Gly-Gly-Phe-Met-Arg-Arg-Val-NH$_2$.

Recent work on the posttranslational proteolytic processing of opioid peptide precursors in the brain has been done on the opioid peptide precursor pro-dynorphin (Kakidani et al., *Nature*, 298, 245-248 (1982)), the processing of which appears to be unusual in that the carboxyltermini of both dynorphin A and dynorphin B (also known as "rimorphin") are released from the precursor by cleavages at single arginine residues rather than at the classical processing sites, paired basic residues. See Docherty et al., *Ann. Rev. Physiol.*, 44, 625-638 (1982). However, classical paired base amino acid cleavages appear to release the vital aminoterminal sequence of the opioids in pro-dynorphin and also the carboxyltermini of alpha-neoendorphin and dynorphin A (Kangawa et al., *Biochem. Biophys. Res. Commun.*, 99, 871-878 (1981); Goldstein et al., *Pnas. U.S.A.*, 78, 7219-7223 (1981)). The peptide according to the present invention appears to be proteolytically derived from pro-enkephalin (Noda et al., *Nature*, 295, 202-206 (1982); Gubler et al., *Nature*, 295, 206-208 (1982); Comb et al., *Nature*, 295, 663-666 (1982)), a second major opioid peptide precursor.

It is therefore an object of the present invention to provide a novel peptide having morphine-like activity.

It is a further object of the present invention to provide methods for isolating and preparing a polypeptide having morphine-like activity.

It is another object of the present invention to provide pharmaceutical compositions useful for alleviating pain.

In the accompanying figures:

FIG. 1 is an HPLC of bovine caudate metorphamide.

FIG. 2 is a graph of the effects of carboxypeptidase A digestion on bovine caudate metorphamide and synthetic dynorphin.

The present invention provides a biologically pure peptide of the form Tyr-Gly-Gly-Phe-Met-Arg-Arg-Val-NH$_2$. This peptide may be isolated from bovine caudate nucleus extracts, detected by a radioaminoassay and purified to homogeneity by gel filtration and reverse phase high performance liquid chromatography. The polypeptide may also be synthesized by the Merrifield solid phase peptide synthesis method.

The peptide according to the present invention may be useful as a pain alleviating drug and has activity similar to that of morphine in that it binds to the μ-binding sites and has a low affinity for the δ-binding site and κ-binding sites. Accordingly, the peptide according to the present invention appears to be unique in its affinity for the μ-binding site, since no other opioid peptide derived from a natural source is known to have such specificity in binding sites.

EXAMPLE 1

Isolation and Characterization of Metorphamide

The starting materials for each of five purifications were about 20 dissected bovine caudate nuclei, approximately 200 g of tissue. The tissue was collected from bovine brains and immediately frozen on dry ice. After weighing, the caudates were homogenized for five minutes in one liter of acid-acetone (acetone:water:12N HCl, 40:6:1) in a Waring blender. The homogenate was spun at 15,000 g for twenty minutes, the supernatant was filtered through gauze and freed from lipid with about 8 liters of heptane. Residual organic solvent was evaporated from the aqueous layer under a stream of nitrogen for 16 hours. The extract, about 150 ml., was neutralized with ammonia, and centrifuged at 15,000 g for twenty minutes. The supernatant was acidified again with glacial acetic acid to a final concentration of 5%, centrifuged again at 15,000 g for twenty minutes and adsorbed to preparative reverse phase C-18 resin (Alltech Associates, particle size 25 μm) equilibrated with 5% acetic acid in a 1.9×7 cm. glass column. After washing with 5% acetic acid, adsorbed peptides were eluted with acid-acetone. Fractions containing peptide material were evaporated with nitrogen and chromatographed on Sephadex G-50 in 50% acetic acid in a 2.5×120 cm. column. Aminoreactive fractions were evaporated with nitrogen, taken up in 5% acetic acid, combined and subjected to two successive reverse phase—HPLC separation systems on an Altex Ultrasphere ODS column (250 ml×4.6 ml., particle size 5 μm). Two HPLC systems were: 50 mM NaH$_2$PO$_4$, 1 ml/l phosphoric acid, 5% methanol, pH 2.7/acetonitrile; and 100 mM Na$_2$HPO$_4$, 5% methanol, pH 7.0/acetonitrile. Peptides were eluted with an acetonitrile gradient as shown in FIG. 1. Purified metorphamide was then desalted on an Altex Ultrasphere Ods column with the following acetonitrile gradient in 0.1% trifluoroacetic acid: 0-15% in 5 minutes, 15-50% in 55 minutes. Flow rate was 1.25 ml/min in all HPLC steps. Amino acid analyses in gas phase sequence determinations were performed as described by Bohlen et al., *Anal. Biochem.*, 26, 144-152 (1982) and Esch et al., *J. Biochem.*, 258, 1806-1812 (1983). The results from the five separate purifications were consistent, each yielding between 200 and 500 pmol. of pure metorphamide. The concentration of metorphamide in crude acid-acetone extracts of bovine caudate nucleus was found to be 12-15 pmol./g. tissue. FIG. 1 shows the optical density and amino reactivity profiles of a typical second RP-HPLC step in the purification of bovine metorphamide. The peptide eluted as a single symmetrical absorbance peak that coincided with the amino reactivity in the metorphamide radioaminoassay. No immunoreactivity or UV-absorbing material eluted between 100 and 180 minutes. The acetonitrile elution gradient was: 0-10% in 10 min., 10-35% in 165 min., 35-50% in 5 min., and 50% for 10 min. The metorphamide-containing peak from the second RP-HPLC step was desalted and chemically characterized by amino acid composition analysis and automated Edman degradation in the gas phase sequencer. Sequence determination gave the following results for the first seven amino acid residues.

TABLE 1

Gas Phase Amino Acid Sequence Analysis of Bovine Caudate Metorphamide

| Cycle No. (N) | PhNCS Amino Acid | Yield (pmoles) | Carryover from (N-1) (pmoles) |
|---|---|---|---|
| 1 | Tyr | 28.5 | — |
| 2 | Gly | 34.0 | 0 |
| 3 | Gly | 21.2 | — |
| 4 | Phe | 29.5 | 6.1 |
| 5 | Met | 35.2 | 0 |
| 6 | Arg | 2.6 | 0 |
| 7 | Arg | 15.8 | — |

TABLE 1-continued
Gas Phase Amino Acid Sequence Analysis of Bovine Caudate Metorphamide

| Cycle No. (N) | PhNCS Amino Acid | Yield (pmoles) | Carryover from (N-1) (pmoles) |
|---|---|---|---|
| 8 | X | — | |

Approximately 200 pmol (by RIA) of bovine metorphamide were loaded on the sequencer. The average repetitive yield was 87.2%.

The complete primary structure of bovine caudate metorphamide was established as: Tyr-Gly-Gly-Phe-Met-Arg-Arg-Val-NH$_2$. The sequence of the first seven amino acids was determined by automated Edman degradation in the gas phase sequencer. The carboxylterminal valine was assigned from amino acid analysis data (Table 2). Carboxylterminal amidation was demonstrated by stability to carboxypeptidase A digestion (FIG. 2) and by full crossreactivity of bovine metorphamide in an RIA requiring the carboxylterminal amide as part of the recognition site.

Amino acid composition analysis showed the presence of 8 amino acid residues, 7 of which were identified during the automated Edman degradation

TABLE 2
Amino Acid Composition Analysis of Bovine Caudate Metorphamide

| Amino Acid | Residues per Molecule | Nearest Integer |
|---|---|---|
| Asx | 0.12 | 0 |
| Thr | 0.10 | 0 |
| Ser | 0.32 | 0 |
| Glx | 0.29 | 0 |
| Gly | 1.93 | 2 |
| Ala | 0.00 | 0 |
| Val | 0.77 | 1 |
| Met | 0.79 | 1 |
| Ile | 0.00 | 0 |
| Leu | 0.15 | 0 |
| Tyr | 0.94 | 1 |
| Phe | 0.83 | 1 |
| His | 0.00 | 0 |
| Trp | 0.00 | 0 |
| Lys | 0.00 | 0 |
| Arg | 1.77 | 2 |
| Cys* | 0.00 | 0 |
| Pro | 0.00 | 0 |
| Total Number of Residues | 8.01 | |

Aliquots of 42 pmol of bovine metorphamide were hydrolized. Values are not corrected for hydrolysis losses and represent averages from two analyses.
*Cys was determined as cysteic acid.

The additional amino acid, valine, is thus assigned to the carboxylterminus.

EXAMPLE 2

Synthesis of Metorphamide

Metorphamide was synthesized on benzhydrylamine resin (0.5 mmole/g) according to the procedures of Matsueda et al., Peptides, 2, 45-50 (1981). The peptide was cleaved from the resin and purified by partition chromatography on Sephadex G-25. The purity was confirmed by thin layer chromatography and reversed phase high performance liquid chromatography. Amino acid analysis further confirmed the correct composition. In the Sephadex G-50 gel filtration chromatography step, the bovine metorphamide-amino reactive material eluted at the same position as I-25 labeled synthetic metorphamide. No higher molecular weight components reacting with the metorphamide antibodies were observed in the fractions eluting from the Sephadex G-50 column. All amino acids used, except Gly, were of the L-configuration.

EXAMPLE 3

Radioaminoassay of Metorphamide

An anti-serum to synthetic metorphamide was generated in male New Zealand white rabbits by injecting synthetic peptide linked to bovine thyroglobulin by carbodiimide according the method of Weber et al., J. Neurochem., 38, 436-447 (1982). The resulting antiserum (R1-3) was used in a radioaminoassay using $^{125}$I labeled synthetic metorphamide as a tracer. The procedure used was as described by Weber et al. with modifications described by Weber et al., Nature, 299, 77-79 (1982). The metorphamide or radioaminoassay requires the carboxylterminal amide group as part of the recognition site. On a molar basis the free carboxy derivative of metorphamide cross reacts with less than 1.02% and the analog of metorphamide in which the carboxyterminal amide was substituted by a Glycine residue cross reacts at less than 0.3%. The adrenal medulla opioid peptides Bam-22 and Bam-12 (Mizuno et al., Biochem. Biophys. Res. Commun., 95, 1482-1488 (1980); Mizuno et al., Biochem. Biophys. Res. Commun., 97, 1283-1290 (1980)) which are carboxyterminal extensions of metorphamide both cross react less than 0.006% in the radioaminoassay.

EXAMPLE 4

Carboxypeptidase A digestion of Bovine Metorphamide and Dynorphin

A mixture of bovine metorphamide (30-35 pmol.) and synthetic dynorphin (60-70 pmol.) was dissolved in 1.6 ml. 0.02 m Tris buffer, containing 0.2 m NaCl and 0.1% Triton X-100, pH 7.5. 5 µl of a 20 mg/ml suspension of carboxypeptidase A ($\sigma$, type 1-DFP) containing 100 µg enzyme were dissolved in 1 ml. 10% LiCl. 4 µl of the freshly prepared solution containing 400 ng enzyme were added to the peptide mixture and a sample was incubated at 37° C. 650 µl aliquots were withdrawn at times 1, 5, 10 and 60 minutes an equal volume of glacial acetic acid was added to each sample to terminate the enzyme reaction. After evaporation, the samples were assayed in triplicate by radioaminoassay for dynorphin and metorphamide. 0 time samples were withdrawn before enzyme was added to determine the amounts of peptides that were initially present in the incubation mixture. A separate sample of peptide mixture that received 4 µl of 10% LiCl without the enzyme was incubated at 37° C. for 60 minutes and 50 µl aliquots of this sample were also assayed for metorphamide and dynorphin. This latter sample served as a control for any non-specific degradation of peptide that may have occurred by unknown factors. No non-specific peptide degradation was observed in the control sample after 60 minutes at 37° C. The results of the digestion are shown in FIG. 2 wherein the metorphamide is indicated by O—O and dynorphin by X—X. Bovine metorphamide was stable to carboxypeptidase A digestion for at least 60 minutes while dynorphin was completely digested by the enzyme after 5 minutes.

EXAMPLE 5

Opioid Bioassays

Bioassays were performed using preparations of the myenteric plexus-longitudinal muscle of the guinea pig and the vasa deferentia of the mouse, rabbit and rat. According to the procedures described by McKnight et al., Eur. J. Pharmacol., 86, 393-402 (1983) and Corbett et al., Nature, 299, 79-81 (1982). The drugs were prepared as 1 mg/ml stock solutions in water and dilutions were made in Krebs solution. The bioassays were performed on [Met 5] enkephalin and C-terminally extended Met 5 enkephalins, and compared with metorphamide. The results are summarized below in Table 3.

TABLE 3

Effect of C-terminally Extended
[Met$^5$]enkephalins in Four Bioassays
$IC_{50}$, nM

| | Guinea-pig Myenteric plexus | Mouse vas deferens | Rat vas deferens | Rabbit vas deferens |
|---|---|---|---|---|
| A* | 6.7** | 1.45** | 260** | >10000 |
| B* | 14.4** | 14.2** | 218** | >10000 |
| C* | 3.28** | 6.4** | 1600** | 126 ± 34 |
| D* | 12.8 ± 6.0 | 12.7 ± 3.1 | >3400 | 31.4 ± 4.1 |
| E* | 6.62 ± 0.8 | 21.4 ± 3.1 | >3000 | 54.7 ± 11.0 |
| F* | 2.46 ± 0.34 | 6.2 ± 1.1 | >3000 | 41.2 ± 4.9 |

*A = [Met$^5$]enkephalin
B = [Met$^5$]enkephalyl-Arg
C = [Met$^5$]enkephalyl-Arg-Arg
D = [Met$^5$]enkephalyl-Arg-Arg-Val
E = [Met$^5$]enkephalyl-Arg-Arg-Gyl
F = [Met$^5$]enkephalyl-Arg-Arg-NH$_2$
**From Bohler et al., Anal. Biochem., 26, 144-152 (1982)

The values shown are the mean±SEM of 4 observations and of 6 for [Met$^5$]enkephalyl-Arg-Arg-Val-Gly. The activity of the peptidases was inhibited by bestatin (10 μM, or 30 μM in the rat and rabbit), L-leucyl-L-leucine (2 nM), thiorphan (0.3 μM) and captopril (10 μM).

Shown above in Table 3 by extending the C-terminal end of Met 5 enkephalin an increase in the activity in the rabbit vas deferens is observed. On the other hand, there is almost a complete loss of activity in the rat vas deferens. In the myenteric plexus and mouse vas deferens the 1, 2 and 3 amino acid extensions on the peptides are nearly aquiactive, however, the 4 amino acid extended peptide and metorphamide are more active in the myenteric plexus than in the mouse deferens.

EXAMPLE 6

Binding Assays

Binding assays were performed in homogenates of guinea pig brain at 0° C. for 150 minutes according the procedure of Corbett et al., supra. [$^3$H]-[D-Ala$^2$,MePhe$^4$, Gly-ol$^5$]enkephalin (1 nM) was used as μ-ligand, [$^3$H]-[D-Ala$^2$,D-Leu$^5$]enkephalin (1 nM) as a relatively selective δ-ligand and [$^3$H]-(—)-bremazocine (0.3 nM) as κ-ligand, in the presence of 100 nM each of unlabelled [D-Ala$^2$,MePhe$^4$,Gly-ol$^5$]enkephalin and [D-Ala$^2$,D-Leu$^5$]enkephalin for the suppression of μ- and δ-binding.

The results are shown below in Table 4.

TABLE 4

Inhibitory Effects of C-terminally extended
[Met$^5$]enkephalin in binding assays

| | $K_I$, nM | | |
|---|---|---|---|
| | I* | II* | III* |
| A** | 9.5 ± 0.54 | 0.91 ± 0.07 | 4442 ± 846 |
| B** | 23.9 ± 3.8 | 16.8 ± 1.8 | 544 ± 22 |
| C** | 3.01 ± 0.75 | 4.42 ± 0.61 | 11.2 ± 1.8 |
| D** | 0.285 ± 0.025 | 4.28 ± 0.89 | 2.11 ± 0.29 |
| E** | 1.39 ± 0.23 | 8.58 ± 1.54 | 6.15 ± 1.13 |
| F** | 0.115 ± 0.019 | 2.65 ± 0.23 | 0.248 ± 0.034 |

*I = [$^3$H]-[D-Ala$^2$,MePhe$^4$,Gly-ol$^5$]enkephalin (μ-site)
II = [$^3$H]-[D-Ala$^2$,D-Leu$^5$]enkephalin (δ-site)
III = [$^3$H]-(-)-bremazocine after suppression of μ-and δ-binding (κ-site)
A = [Met$^5$]enkephalin
B = [Met$^5$]enkephalyl-Arg
C = [Met$^5$]enkephalyl-Arg-Arg
D = [Met$^5$]enkephalyl-Arg-Arg-Val
E = [Met$^5$]enkephalyl-Arg-Arg-Gyl
F = [Met$^5$]enkephalyl-Arg-Arg-NH$_2$ The values shown are the mean ±SEM of three to five observations. The assays used homogenates of guinea-pig brain incubated for 150 minutes at 0° C. The μ- and w-binding of [$^3$H]-(—)-bremazocine was suppressed with 100 nM each of unlabelled [D-Ala$^2$,MePhe$^4$,Gly-ol$^5$]enkephalin and [D-Ala$^2$,D-Leu$^5$]enkephalin.

In the binding assays, any extension of the peptide beyond the pentapeptide abolishes δ-selectivity (Table 4). The addition of Arg$^6$ introduces some affinity at the κ-site. Addition of Arg$^6$-Arg$^7$ leads to a marked increase in affinity at all three sites but especially at the κ-site. Further extension at the C-terminus, Arg$^6$-Arg$^7$-Val$^8$, increases affinity at the μ- and κ-sites but not at the δ-site; the addition of Gly$^9$ somewhat reduces affinity at all three sites. Amidation of Val$^8$ (metorphamide) causes an increase in κ-affinity with only little change at the two other sites. Thus, at $K_D$ concentrations of the tritiated ligands metorphamide is a potent μ-agonist with relative potencies of 0.66 at the μ-site, 0.03 at the δ-site and 0.31 at the κ-site whereas the respective values of the non-amidated peptide are 0.83, 0.06 and 0.11 (total binding=1).

Metorphamide and its pharmaceutically acceptable salts are useful for alleviating pain and are suitable substitutes for conventional opioids such as morphine. Since morphine also exhibits a high affinity for the μ-binding site, the dosages which metorphamide may be readily determined by comparing the relative binding affinities of morphine versus metorphamide. The relative affinities for morphine are 0.97 for the μ-binding site, 0.02δ for the δ-binding site and 0.01κ for the κ-binding site. The values for metorphamide are 0.66μ, 0.03δ and 0.31κ. Therefore, the activity of metorphamide for the μ-binding site is approximately ⅔ of that of morphine. Metorphamide may be admixed with conventional pharmaceutical carriers, such as saline, or may be formed into pellets, capsules, salves and the like. Preferably, metorphamide will be administered intravenously.

What is claimed is:

1. A biologically pure polypeptide of the formula Tyr-Gly-Gly-Phe-Met-Arg-Arg-Val-NH$_2$.

2. The method for alleviating pain in mammals comprising the step of administering to said mammal an effective amount of a compound of the structure Tyr-Gly-Gly-Phe-Met-Arg-Arg-Val-NH$_2$.

3. A pain alleviating composition comprising a polypeptide of the formula Tyr-Gly-Gly-Phe-Met-Arg-Arg-Val-NH$_2$ or a pharmaceutically acceptable salt thereof in a pharmaceutically acceptable carrier.

* * * * *

UNITED STATES PATENT AND TRADEMARK OFFICE
CERTIFICATE OF CORRECTION

PATENT NO. : 4,490,363
DATED : December 25, 1984
INVENTOR(S) : Jack D. Barchas; Eckard Weber; Christopher J. Evans It is certified that error appears in the above-identified patent and that said Letters Patent is hereby corrected as shown below:

In column 5, line 43, the word "aquiactive" should read "equiactive".

Signed and Sealed this

Tenth Day of September 1985

[SEAL]

Attest:

DONALD J. QUIGG

Attesting Officer     Acting Commissioner of Patents and Trademarks - Designate

UNITED STATES PATENT AND TRADEMARK OFFICE
CERTIFICATE OF CORRECTION

PATENT NO. : 4,490,363
DATED : December 25, 1984
INVENTOR(S) : Barchas, et al.

It is certified that error appears in the above—identified patent and that said Letters Patent is hereby corrected as shown below:

In column 1, insert the following as the first paragraph:

This invention was made in the course of work under NIMH Grant 5R01 DA-01207 from the National Institute of Drug Abuse and under Contract No. N00014-79-C-0796 from the Office of Naval Research. The United States Government has rights to the invention pursuant to these funding agreements.

Signed and Sealed this

Ninth Day of December, 1986

*Attest:*

DONALD J. QUIGG

*Attesting Officer*  *Commissioner of Patents and Trademarks*